United States Patent [19]

Laico et al.

[11] Patent Number: 5,025,802

[45] Date of Patent: Jun. 25, 1991

[54] SURGICAL HOLDING APPARATUS FOR DISTRACTING ANKLE

[75] Inventors: Joseph P. Laico, New City; Joseph L. Molino, Valley Cottage, both of N.Y.

[73] Assignee: Lincoln Mills, Inc., New City, N.Y.

[21] Appl. No.: 477,319

[22] Filed: Feb. 8, 1990

[51] Int. Cl.[5] .......................... A61F 5/37; A61F 5/04; A61H 1/02

[52] U.S. Cl. .................................. 128/882; 128/84 R; 128/75; 128/875

[58] Field of Search ...................... 128/75, 84 A, 84 B, 128/84 C, 87 R, 87 C, 85, 882, 54, 84 R, 77, 80 R, 875, 165, 166, 846; 606/54, 57; 269/328

[56] References Cited

U.S. PATENT DOCUMENTS

| | | | |
|---|---|---|---|
| 488,631 | 12/1892 | King | 128/84 R |
| 3,087,489 | 4/1963 | Gilbert et al. | 128/84 R |
| 3,135,257 | 6/1964 | Anderson | 128/84 R |
| 3,720,206 | 3/1973 | Walker et al. | 128/75 X |
| 3,850,165 | 11/1974 | Throner | 128/80 C |
| 4,350,153 | 9/1982 | Borschneck | 128/84 C |
| 4,641,637 | 2/1987 | Rosen | 128/75 |
| 4,782,827 | 11/1988 | Paratte | 128/80 R |

*Primary Examiner*—Robert A. Hafer

*Assistant Examiner*—Michael Brown

*Attorney, Agent, or Firm*—Chilton, Alix & Van Kirk

[57] ABSTRACT

A limb holding apparatus mounts to the rails of an operating table for distracting the ankle of a patient for surgery and like procedures. The ankle of the patient is attached by a harness to a traction applicator. The traction applicator can be variably adjusted in terms of both direction and applied force for applying traction to the ankle joint. The apparatus is readily adjustable for repositioning the limb of the patient.

17 Claims, 3 Drawing Sheets

SURGICAL HOLDING APPARATUS FOR DISTRACTING ANKLE

BACKGROUND OF THE INVENTION

1. Field of the Invention

This invention relates generally to an apparatus adapted for immobilizing the limbs of a patient during surgery or the like. More particularly, the present invention relates to apparatus for holding the leg and foot of a patient surgery for distracting the ankle joint during arthroscopic surgery or other surgical procedures.

Limb supporting devices to which the invention relates require that the extremity or limb involved in surgery be effectively immobilized by an apparatus which also allows for the limb to be repositioned at a different orientation when required and then be firmly immobilized at the new position. The apparatus must also be adapted to efficiently allow the joint, which is involved in the surgery, to be distracted to a selected position to thereby allow insertion of surgical instruments or the like.

2. Description of the Prior Art

A number of devices have been advanced for immobilizing limbs during surgery or therapeutic procedures. Many of the conventional limb holding devices are cumbersome and not easily used during surgical procedures. In addition, many of the conventional devices have a limited range of positions at which the limb portion being treated may be repositioned. Naturally, the surgeon can most efficiently and effectively treat a patient if the device provides a wide repositioning range and also provides an efficient means for firmly immobilizing the limb to be treated at the desired position.

International PCT application PCT/US89/01660 published on Nov. 2, 1989, discloses a limb supporting device which was invented by the inventors of the present invention. The limb holding device is designed to be attached to an operating table to immobilize the arm or leg of the patient during arthoscopic surgery or the like. The limb supporting device is particularly adapted for distraction of the hip joint. The device includes a pair of vertical upright supports, which are braced by an adjustable connecting bar, and a fork-like member which is mounted between a pair of tines to form a cradle. A plurality of straps on the cradle immobilize the patient's limb. A handle is employed to facilitate manipulation of the limb to thereby place the proper traction on the limb. A tension meter is intergrated into the fork-like member to allow direct and accurate indication of the traction force which is placed on the limb.

Other limb supporting devices, which are generally pertinent to the present invention are disclosed in the following references:

| Patentee | U.S. Pat. No. |
|---|---|
| H. Gilbert et al | 3,087,489 |
| Tammy et al | 3,840,166 |
| Reed | 4,551,872 |
| Whitehead et al | 4,649,907 |
| Jacobsen | 4,483,330 |
| Invidiato | 2,302,868 |

SUMMARY OF THE INVENTION

Briefly stated, the invention in a preferred form is a limb holding apparatus which may be employed for distracting the ankle joint during surgery or like procedures. The apparatus is adapted for mounting to the rails of an operating table. The apparatus functions to immobilize the leg and foot of the patient in an efficient, firm fashion while also providing a high degree of flexibility in the direction of the traction force applied to the foreleg and ankle, so as to achieve a proper distraction of the ankle joint during surgery.

The limb holding apparatus is employed in connection with an operating table having transversely spaced, longitudinal rails which extend at opposing sides of the table. A leg support assembly is clampable to the rails and engageable with the leg of the patient, such as at the underside of the knee, for supporting the leg above the operating table. A foot assembly, which holds the foot of the patient, comprises a harness which attaches to the ankle of the patient. The leg support assembly may comprise a generally U-shaped member and a roll pad, which is mounted to the member. A pair of table clamps are employed for mounting the U-shaped member to the rails and also for adjusting the vertical height of the member relative to the operating table. The leg support assembly may also comprise a pair of uprights which support a cross member.

An applicator for applying a traction force to the harness is mounted to one of the rails. The traction applicator includes a mechanism for adjustably positioning the applicator so that the traction force vector may be applied to the harness at a selected direction. A scale is employed for indicating the traction force which is applied to the harness. The traction force may be variably adjusted by means of a handle which rotatably controls the axial position of a shaft displaceable from a housing. A cable controlled by the shaft connects to the foot harness.

The foot assembly may also employ a table clamp to mount the assembly to one of the operating table rails. In one embodiment a connector strut and a cross bar connect to mount the traction applicator housing. The positions of the connector strut and the applicator housing are adjustable for selectively controlling the direction of the applied traction force.

The foot harness includes a strap forming a pair of interconnected loops. Pads are attached to the loops for engaging the rear and top of the foot. The harness is slipped onto the foot. A traction force applied to an end portion of the strap exerts a force against the top and back of the foot to distract the ankle joint.

An object of the invention is to provide a new and improved holding apparatus for distracting an ankle for surgery or the like.

Another object of the invention is to provide a new and improved apparatus of efficient and low cost construction which is efficiently adaptable for use during surgery to immobilize the leg and foot of a patient.

A further object of the invention is to provide a new and improved surgical apparatus which is capable of positioning and repositioning the leg and foot at a wide spectrum of selected fixed positions.

Other objects and advantages of the invention will become apparent from the drawings and the specification.

DESCRIPTION OF THE PREFERRED EMBODIMENT

Figure 1:
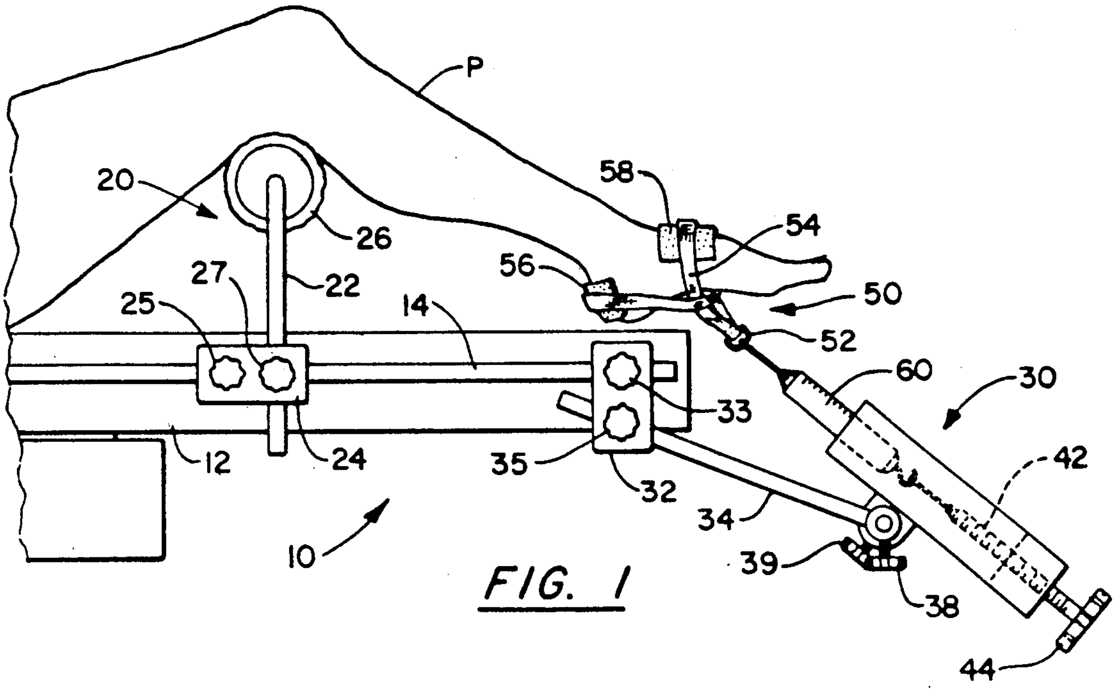
FIG. 1 is a side elevational view, partly in phantom, of a surgical holding apparatus of the present invention and a portion of an associated operating table illustrated in conjunction with a limb of a patient.
Figure 2:
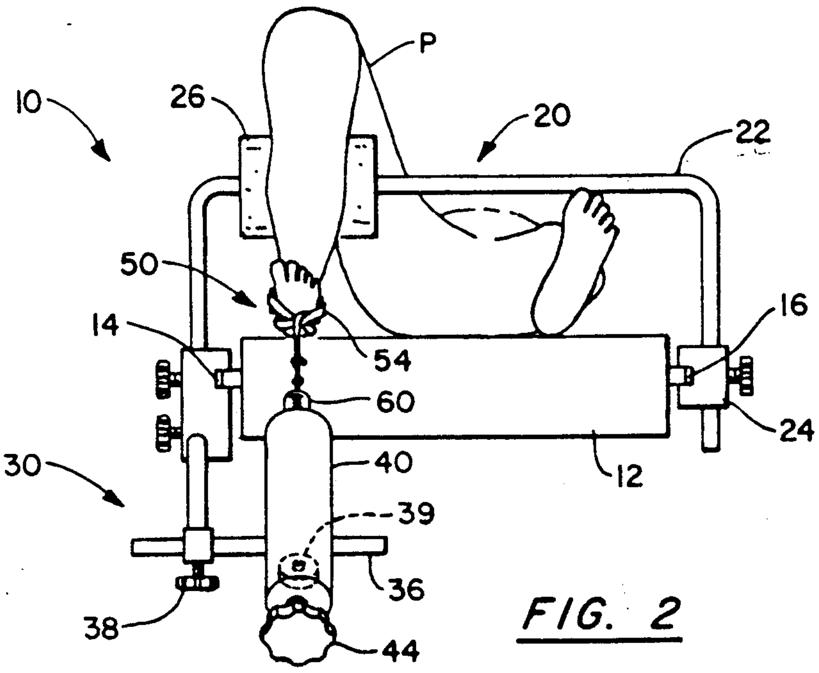
FIG. 2 is an end view of the surgical holding apparatus, operating table and patient of FIG. 1.

With reference to the drawings, wherein like numerals represent like parts throughout the figures, a holding apparatus for distracting an ankle joint for surgery and like procedures is generally designated by the numeral 10. Holding apparatus 10 is mountable to a conventional operating table 12 of a type having opposed transversely spaced side rails 14 and 16 which extend longitudinally at the sides of the operating table. Holding apparatus 10 functions to secure and support the leg and foot of a patient in an immobilized distracted state so that the ankle joint of the patient may be properly positioned for arthroscopic surgery or other procedures. As will be detailed hereinafter, the holding apparatus 10 provides a very advantageous feature wherein the leg and foot may be effectively immobilized in an efficient manner while also readily permitting repositioning of the limb as desired. The apparatus 10 also applies the proper distracting force during the surgery.

The holding apparatus 10 comprises a leg support 20 and a cooperative foot assembly designated generally by the numeral 30. The leg support 20 and the foot assembly 30 are independently mountable to the operating table 12. The leg support 20 mounts to rails 14 and 16, and the foot assembly 30 mounts to side rail 14. The leg support 20 and the foot assembly 30 are independently longitudinally positionable on the rails.

The patient P is positioned in a reclined position on the operating table 12. The leg support 20 engages the underside of the patient's knee. Other positions of the patient and other engagements locations of the leg support are also possible. The foot assembly 30 is attached to the patient's foot and cooperates with the leg support 20 to provide the ankle joint distraction as will be detailed hereinafter.

Leg support 20 which may have the form of a conventional perineal bar comprises a generally inverted U-shaped, ⅞ inch steel bar upright 22. The upright is mounted at a selected fixed longitudinal position by a pair of slidable table clamps 24 clampable to each of the side rails 14 and 16. The clamps 24 each carry a clamp screw 25 for clamping against the rails and a second clamp screw 27 for clamping against the legs of the upright. The upright 22 is thus both vertically and longitudinally positionable relative to the operating table to provide the proper vertical height and longitudinal position for supporting the patient's leg at the desired position above the operating table. A well padded bolster 26 is mounted to the cross-portion of the upright. The bolster 26 is dimensioned and transversely positionable to engage the underside of the knee or other suitable leg location of the patient. Alternately, the bolster 26 may extend substantially the entire transverse width of the upright cross portion.

The foot assembly 30 includes a slidable table clamp 32 which is fixably positionable along rail 14 of the operating table. An angularly adjustable connector strut 34 extends obliquely relative to the table clamp 32 (in the drawing) in a direction which may be generally described as forwardly and downwardly relative to the operating table. Table clamp 32 carries a clamp screw 33 for clamping against the rail 14 and a second clamp screw 35 for clamping the connector strut at a fixed angle to the rail. The angular position of the connector strut may be selectively fixed as desired and secured by tightening clamp screw 35. A cross bar 36 is connected at the distal end portion of the connector strut by means of a connector 38. The cross bar 36 extends generally orthogonally to the strut 34. The connector 38 includes a clamp mechanism for fixing the cross bar at a selected fixed transverse position relative to the strut (and the operating table). The operating table can also be repositioned while the foot assembly remains fixed relative to the rail to obtain the desired position.

The cross bar 36 pivotally mounts a traction applicator comprising a cylindrical housing 40. The applicator is angularly positionable about cross bar 36 and clamped at a selected fixed position by clamp screw 39. The cylindrical housing 40 encloses a variably axially positionable shaft 42, the position of which relative to the housing 40, is controlled by a handle 44. Rotatable motion of the handle 44 is translated into corresponding axial displacement of the shaft 42.

Figure 3:
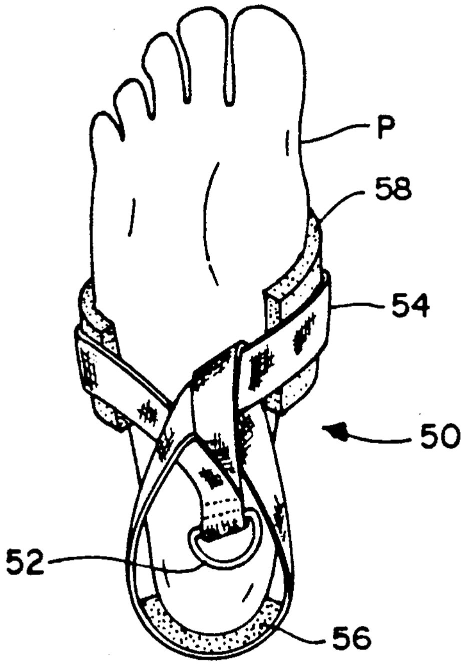
FIG. 3 is an enlarged bottom view of the foot holding portion of the surgical holding apparatus of FIG. 1 illustrated in conjunction with the foot of a patient.

With additional reference to FIG. 3, a foot sling or harness 50 is adapted for attachment to the foot of the patient. The harness 50 terminates in a ring 52. A tension scale 60 or traction force indicator, which may be a fish scale or other suitable spring scale, has a hook which is received in the ring 52. The opposing end of the scale is connected with the distal end of the shaft 42. The scale 60 may be graduated in either pounds or kilograms and is employed for continuously monitoring the amount of the distracting force which is applied to the ankle of the patient.

The foot harness 50 includes a strap 54 of nylon webbing or other suitable material which engages an intermediate bottom location of the foot and wraps around the back of the foot. A foam pad 56 is attached to the strap for engagement against the back of the foot. A foam pad 58 is also attached to the strap for engagement against the top of the foot. The terminus of the strap is stitched to form a loop for attaching ring 52. In the attached mode configuration illustrated in FIG. 3, the lead strap segment continues from ring 52 loops over itself at the bottom of the foot and wraps around the back of the foot where attached pad 56 conformally engages the back of the foot. The strap wraps to the bottom of the foot, crosses on itself, loops through itself and continues across the top of the foot where attached pad 58 conformally engages the top of the foot. The strap then extends to the bottom of the foot where it loops under the strap and reconnects with the lead segment of the strap to form the loop for ring 52. The harness 50 easily attaches to the foot and is comfortable to the patient. The multiple looped wrapped configuration as described effectively distributes the traction force applied to the harness to exert a distracting force through pads 56 and 58. The harness 50 self-adjusts to the foot size of the patient.

It will be appreciated that the leg support 20 and the foot assembly 30 are easily selectively slidably positionable along the side rail 14 of the operating table. The vertical height of the upright 22 is adjusted and clamped via table clamp 24 at the desired position. The bolster 26 is also transversely positioned. The ankle sling or harness 50 is slipped onto the foot of the patient and connected to the tension scale 60. The shaft 42 is initially positioned at an intermediate axial position. The strut 34 and the cross bar 36 are positioned as desired. The housing 40 is angularly and transversely oriented to obtain the proper limb position and direction of the distracting vector force applied to the foreleg. The clamp screw 39 is then tightened to fix the selected position of the housing 40.

The appropriate tension vector or distracting force is applied by appropriately turning the handle 44 which activates a screw drive mechanism for varying the tension or distracting force applied to the ankle. The scale 60 allows the surgery room personnel or the physician to continuously monitor the amount of distraction force applied to the joint. In the immobilized position depicted in the drawings, the leg and foot of the patient are essentially immobilized and a controlled distracting force is applied at the selected orientation of the limb. It should, however, be appreciated that should a different limb position be desired during the surgery, the new position can be relatively easily obtained by appropriately adjusting one or more positions which include the angular position of the applicator housing 40, the longitudinal position of the foot assembly 30 (table clamp 32), the angular position of the connector strut 34, the transverse position of the cross bar 36, the longitudinal position of the leg support 20, and the vertical height of the leg support 20. In addition, the distracting force applied to the ankle can be variably adjusted via the handle 44.

Figure 4:
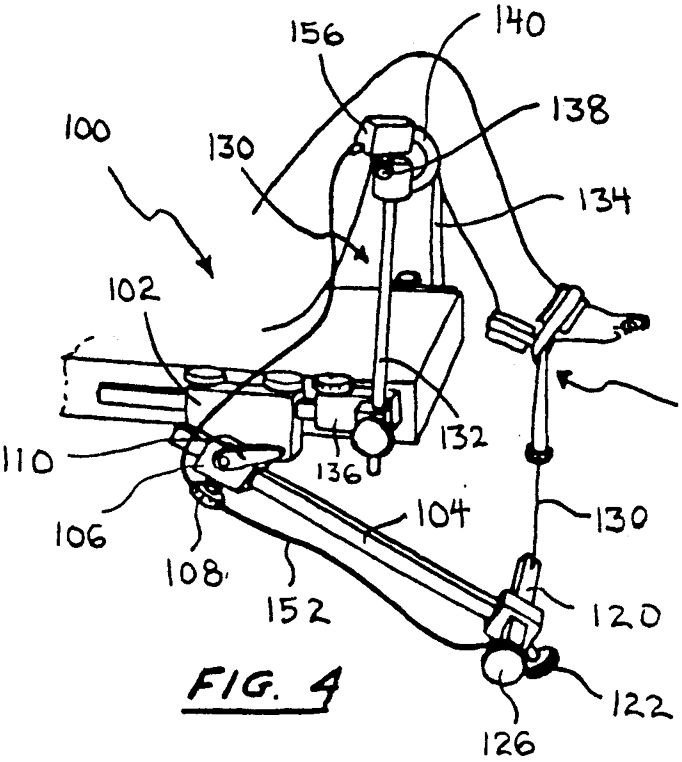
FIG. 4 is a perspective view of another embodiment of a surgical holding apparatus of the present invention and a portion of an associated operating table illustrated in conjunction with a limb of a patient.
Figure 5:
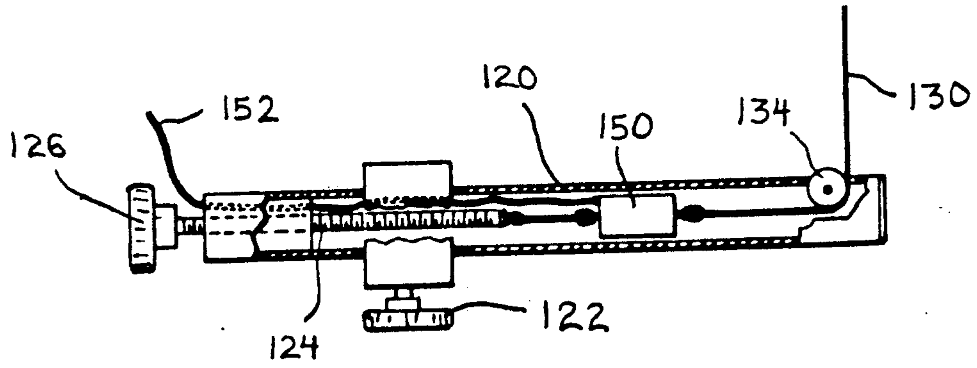
FIG. 5 is an enlarged sectional view, partly broken away and partly in schematic, of the surgical holding apparatus of FIG. 4.

With reference to FIGS. 4 and 5, another embodiment of a limb holding apparatus in accordance with the present invention, is generally designated by the numeral 100. A table clamp 102 is longitudinally positionable and clampable at a fixed longitudinal position to a rail of a standard operating table. A strut 104 extends from the table clamp in a variably positionable orientation which is ordinarily generally forwardly and downwardly from the operating table, as illustrated in FIG. 4. The strut, which may be a 1 inch stainless steel tube, is axially slidable through a sleeve 106 and clamped at the desired axial position by a clamp screw 108. The sleeve 106 is pivotally mounted to the table clamp so that the strut is angularly positionable at the desired angular position and locked in place by a clamp lever 110.

An applicator housing 120 which is generally constructed of a 1¼ inch square stainless steel tube, is mounted at the distal end of the strut. The housing is transversely positionable relative to the strut 104 and secured in the desired transverse position by means of a clamp screw 122. With additional reference to FIG. 5, the applicator comprises an axially positionable shaft 124. The axial position of the shaft 124 is controlled by a rotatable knob 126 located at one end of the housing. The shaft controls the extensive position of a cable 130 which extends around a pully 134 and projects through an aperture of the housing. The cable connects with the foot harness 50 which is substantially identical to that previously described. The traction force which is applied to the harness is variably adjusted by means of angular displacement of the knob 126.

The leg assembly 130 comprises a pair of uprights 132 and 134 which are mounted by a table clamps 136 to the operating table rails. The uprights support cross bar 138, the position of which is longitudinally and vertically adjustable by means of the table clamp. A padded bolster 140 is mounted to the cross bar.

A tensiometer 150, which may be a load cell or other suitable device for sensing the tension force, is mounted within the housing for sensing the tension applied to the cable. An electrical lead 152 extends from the tensiometer to a readout indicator 156 which is mounted to upright 132. The distracting force applied to the ankle may thus be continuously monitored by visual inspection of the indicator 156. The indicator may provide a readout in pounds, kilograms or other suitable units and is powered by a 9 volt battery.

Both limb holding apparatus 10 and limb holding apparatus 100 thus provide an efficient means for distracting the ankle joint to provide access for surgical instruments. The immobilization of the limb is accomplished with a very efficient structure which is easily adjusted to provide a new angle or position for the joint—especially if repositioning is required during the surgical procedure. Moreover, the optimum position of the limb of the patient can be easily obtained by appropriate adjustment of the apparatus as previously described. In some instances, repositioning of the limb is obtained by repositioning moveable sections of the operating table while fixedly maintaining the position of the holding apparatus. The tension scale 60 or tensiometer indicator 150 is readily visible to provide for continuous monitoring of the traction applied to the limb.

While a preferred embodiment of the foregoing invention has been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. Apparatus for holding the leg and foot of a patient for surgery and the like comprising:

operating table means comprising a table and a pair of transversely spaced, longitudinal rails extending at opposing sides of said table;

leg support means clampable to said rails and engageable with the leg of the patient for supporting the leg of the patient above the operating table so that said foot is suspended at a first height; and foot assembly means for holding the foot of the patient comprising:

harness means for attachment to the foot of the patient comprising first and second interconnected engagement means for engagement against the respective top and back portions of the foot;

traction applicator means for applying a traction force to said harness means;

mounting means for mounting said traction applicator means to a rail for positioning said traction applicator means generally below said first height; and direction selector means for adjustably positioning said traction applicator means for applying a traction force to said harness means at a selected direction, so that a patient may be positioned on said table means with the leg engaged by the leg support means for suspending the foot, and the harness means mounted to the foot, wherein a traction force applied by the applicator means exerts a force which is distributed through said first and second engagement means against the top and back portions of the foot to distract the angle joint.

2. The apparatus of claim 1 further comprising indicator means for indicating the traction force applied to the harness means.

3. The apparatus of claim 2 wherein said indicator means comprises a spring actuated scale disposed between said harness means and said applicator means.

4. The apparatus of claim 1 wherein said traction applicator means further comprises adjustment means for varying the traction force applied by said applicator means.

5. The apparatus of claim 4 wherein said traction applicator means further comprises a housing, a shaft and handle means for rotatable actuation to axially displace said shaft relative to said housing.

6. The apparatus of claim 1 further comprising a cable connecting said harness means, said cable being displaceable in response to displacement of said shaft.

7. The apparatus of claim 1 wherein said mounting means comprises a table clamp and a strut extending from said table clamp.

8. The apparatus of claim 1 wherein said direction selector means comprises means for fixing the position of the strut at a selected angle relative to the table clamp.

9. The apparatus of claim 1 wherein said leg support means comprises a pair of uprights, a cross member supported on said uprights and a rolled pad mounted to said member.

10. The apparatus of claim 1 wherein said harness means comprises a strap forming a pair of interconnected loops, a pad being mounted to each loop.

11. The apparatus of claim 1 wherein said harness means comprises a strap defining a pair of interconnected loops, a portion of each loop passing through the other loop, one loop dimensioned to extend about the back of the foot and the other loop dimensioned to extend about the top of the foot.

12. Surgical apparatus for holding the leg and foot of a patient positioned on an operating table comprising:

leg support means engageable with the leg of the patient for supporting the leg;

foot assembly means comprising:

harness means for attachment to the foot of the patient comprising a single continuous strap defining a pair of interconnected loops, a portion of each loop passing through the other loop, one loop dimensioned to extend about the back of the foot and the other loop dimensioned to extend about the top of the foot;

traction applicator means for applying a traction force to said harness means, said traction applicator means comprising adjustment means for variably adjusting the traction force;

mounting means comprising a strut for mounting said traction applicator means to the operating table;

direction selector means comprising first means for adjusting the angular position of said strut and second means for adjusting the position of said traction applicator means in relation to said strut for applying a traction force to said harness means at a selected fixed direction, so that said traction force is distributable to said loops to distract the ankle joint of the foot.

13. The surgical apparatus of claim 12 further comprising traction sensing means disposed between said harness means and said traction applicator means for sensing the traction force applied to said harness means.

14. The surgical apparatus of claim 12 wherein said traction applicator means comprises a housing and handle means disposed exteriorly of said housing for rotatable displacement to vary the force applied to the harness means.

15. The surgical apparatus of claim 12 wherein the mounting means further comprises a table clamp.

16. The surgical apparatus of claim 12 wherein the leg support means comprises a pair of uprights mounted by a pair of table clamps and a cross member supported by said uprights.

17. The surgical apparatus of claim 16 further comprising height adjustment means for variably adjusting the vertical height of said cross member relative to the operating table.

* * * * *